United States Patent
Scholz et al.

(10) Patent No.: US 6,482,992 B2
(45) Date of Patent: Nov. 19, 2002

(54) MULTISTAGE PROCESS FOR THE PREPARATION OF OXO ALDEHYDES AND/OR ALCOHOLS

(75) Inventors: Bernhard Scholz, Marl (DE); Franz Nierlich, Marl (DE); Alfred Kaizik, Marl (DE); Dieter Hess, Marl (DE); Wilfried Bueschken, Haltern (DE); Klaus-Diether Wiese, Haltern (DE); Dirk Roettger, Recklinghausen (DE); Guido Protzmann, Marl (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 09/904,893

(22) Filed: Jul. 16, 2001

(65) Prior Publication Data

US 2002/0028974 A1 Mar. 7, 2002

(30) Foreign Application Priority Data

Jul. 14, 2000 (DE) .......................... 100 34 360

(51) Int. Cl.⁷ ............................................. C07C 45/50
(52) U.S. Cl. .................... 568/451; 568/454; 568/909
(58) Field of Search ................. 568/429, 451, 568/454, 909

(56) References Cited

U.S. PATENT DOCUMENTS 3,868,422 A * 2/1975 Hart et al. ............ 260/604 HF
6,015,928 A * 1/2000 Gubisch et al. ............. 568/882

* cited by examiner

*Primary Examiner*—Sreeni Padmanabhan
(74) *Attorney, Agent, or Firm*—Oblon, Spivak, McClelland, Maier & Neustadt, P.C.

(57) ABSTRACT

Olefins are hydroformylated to give alcohols and/or aldehydes in a plurality of hydroformylation stages, each of which comprises:

a) hydroformylating olefins having a carbon atom content of 6 to 24 carbon atoms in the presence of a cobalt- or rhodium catalyst in a reactor to the point of conversion of olefin reactant to product of 20 to 98%;

b) removing the catalyst from the resulting liquid discharged from the reactor;

c) separating the resulting liquid hydroformylation mixture into a low-boiler fraction comprising olefins and paraffins, and a bottoms fraction comprising aldehydes and/or alcohols; and d) reacting the olefins present in the low-boiler fraction in subsequent process stages comprising steps a, b and c and combining the bottoms fractions of process steps c) of all process stages.

19 Claims, 3 Drawing Sheets

MULTISTAGE PROCESS FOR THE PREPARATION OF OXO ALDEHYDES AND/OR ALCOHOLS

BACKGROUND OF THE INVENTION

1. Field of the Invention

The present invention relates to a process for the preparation of aldehydes having 7 to 25 carbon atoms by multistage cobalt- or rhodium-catalyzed hydroformylation of the corresponding olefins.

2. Description of the Background

As is known, higher aldehydes, in particular those having 7 to 25 carbon atoms, can be prepared by catalytic hydroformylation (referred to as the oxo process) of the olefins which have one fewer carbon atom. The aldehydes are used, for example, as precursors for the production of carboxylic acids and as fragrances. In industry they are often converted into the corresponding alcohols by catalytic hydrogenation, such alcohols being used inter alia as intermediates for the preparation of plasticizers and detergents.

A large number of processes for the hydroformylation of olefins is described in the literature. The choice of catalyst system and optimal reaction conditions for the hydroformylation are dependent on the reactivity of the olefin used. The effect of the structure of the olefin on its reactivity in the hydroformylation reaction is described, for example, by J. FALBE, *New Syntheses with Carbon Monoxide"*, Springer Verlag, 1980, Berlin, Heidelberg, New York, pages 95 et seq.

As a general rule, the rate of hydroformylation reactions under constant general conditions decreases with increasing carbon number and with increasing degree of branching of the olefin. Thus, the reaction rate of linear olefins can exceed that of the branched isomers by more than a factor of ten. In addition, the position of the double bond in the olefin has a decisive influence on the reactivity. Olefins with a terminal double bond react markedly more quickly than isomers with the double bond inside the molecule. The varying reactivity of isomeric octenes has been investigated, for example, by B. L. Haymore, A. van Hasselt, R. Beck, *Annals of the New York Acad. Sci.*, 1983, 415, 159–175. A general overview and further literature are given by B. Cornils, W. A. Herrmann, *"Applied Homogeneous Catalysis with Organometallic Compounds"*, Vol. 1&2, VCH, Weinheim, New York, 1996.

Industrial olefin mixtures which are used as starting materials for the hydroformylation synthesis often contain olefin isomers of very different structures having differing degrees of branching and different double bond positions, and olefins of varying molecular weights. This is true in particular of olefin mixtures produced by di-, tri- or continuing oligomerization of olefins having 2 to 8 carbon atoms or other readily accessible higher olefins, or by cooligomerization of the olefins. Possible examples of typical olefin mixtures which are relevant industrially for the hydroformylation reaction are tri- and tetrapropene, and di-, tri- and tetrabutenes.

In the case of a hydroformylation reaction conducted on an industrial level, it is desired to achieve, in addition to a high conversion, a high selectivity in order to ensure optimal utilization of the raw material. To achieve a high conversion, in the case of olefins which react slowly, a relatively long reaction time and/or relatively high reaction temperatures must often be accepted. By contrast, more reactive olefins are converted to the aldehydes under the same reaction conditions in a much shorter time. If mixtures of olefins of varying reactivity are hydroformylated together, this leads to the need for relatively long reaction times in order to achieve adequate conversion also of the olefins which are more difficult to hydroformylate. However, the aldehydes produced from olefins which can be more readily converted are formed relatively quickly and are then present in the reactor alongside the olefins which are more difficult to hydroformylate. This leads to undesired secondary and consecutive reactions of the aldehydes, e.g. to hydrogenation, to condensation reactions and to the formation of acetals and hemiacetals. Primarily because of the varying reactivity of the olefin isomers, it is therefore difficult to achieve high conversions and also high selectivities during the hydroformylation reaction.

As well as the disadvantageous effect on the selectivity of the reaction, there are two other aspects of the hydroformylation reaction which mitigate against a joint hydroformylation of olefin mixtures in one stage to achieve high conversions. First, the relatively long reaction times for a pregiven capacity (or reactor performance) require relatively large reactor volumes. This is a distinct disadvantage, particularly since hydroformylation processes are processes which occur at increased pressure, and the investment costs for pressurized reactors increase exponentially with size. Secondly, control of the product properties of the aldehydes is limited, e.g. determined by the n/i ratio.

Processes for the two-stage hydroformylation of olefins are known. EP 562 451 and EP 0 646 563 describe the hydroformylation of mixtures comprising 1- and 2-butene where, in the first stage, the 1-butene is reacted in a heterogeneous reaction, i.e. in a multiphase system, optionally with the addition of a phase transfer reagent or solubility promoter and, in the second stage, a homogeneous, dissolved catalyst is used. According to EP 0 562 451, rhodium catalysts are used in both stages, while according to EP 0 646 563, rhodium catalysts are used in the first stage and cobalt catalysts are used in the second stage. According to EP 0 562 451, the olefin which is unreacted in the first stage, largely 2-butene, is hydroformylated in a second stage in a homogeneous phase and in the presence of rhodium as catalyst. In EP 0 646 563 this procedure is specified inasmuch as the unreacted olefin in the first stage leaves the reactor in gaseous form, together with carbon monoxide, hydrogen and butane produced by hydrogenation. This gas, optionally at compression, is passed to the second hydroformylation stage. The procedure of these two publications cannot be used with advantage for the hydroformylation of higher olefins, i.e. olefins having more than 5 carbon atoms, because the unreacted olefins can no longer be discharged in gaseous form from the first stage with viable expenditure because of their relatively high boiling points.

GB 1 387 657 describes a two-stage hydroformylation reaction in which the reaction product from the first stage is discharged in gaseous form and, after the aldehydes or alcohols have been removed by condensation, some of the off-gas from the first stage, which comprises unreacted olefins, is returned to the first stage, and the remainder is passed to the second reactor. This process concept is suitable for the hydroformylation of volatile olefins having no more than 5 carbon atoms, e.g. for ethylene or propylene. Like the processes mentioned above, this procedure is not advantageous for the reaction of higher olefins, since the vapor pressures of the olefins (and those of the aldehydes) are too low and the process therefore has to inevitably be conducted in the liquid phase.

WO 95/08525 describes a two-stage hydroformylation process in which the reaction mixture is discharged from the first stage as a gas. Allegedly, olefins having 2 to 20 carbon atoms, in particular 2 to 8 carbon atoms, can undergo reaction by the process. The hydroformylation is rhodium-catalyzed, and the catalyst is identical in both stages. The example describes the hydroformylation of propylene. As with the processes described above, higher olefins having more than 5 carbon atoms cannot be converted with advantage to hydroformylation product on an industrial scale because of the relatively high boiling points of the starting materials and products. Conversion in the gas phase is therefore energetically unfavorable.

A further variant of a two-stage hydroformylation process is described in DE 3 232 557. In the first stage, the olefins are hydroformylated using a cobalt catalyst and conversions of 50–90% are achieved, the cobalt catalyst is separated from the reaction mixture, and the aldehydes formed are introduced into a second hydroformylation stage together with the unreacted olefins. The ligand-modified cobalt catalyst used here affects not only further hydroformylation of the olefins, but also hydrogenation of the aldehydes to give the alcohols. In addition, the aldehydes produced in the first stage are exposed to the energetic reaction conditions of the second stage. This leads to consecutive reactions, in particular, to condensation reactions with the formation of high-boiling components.

SUMMARY OF THE INVENTION

Accordingly, one object of the invention is to provide a process for the preparation of higher oxo aldehydes or the corresponding alcohols from olefins or olefin mixtures which simultaneously achieves high conversions of olefin (s)with high selectivities to product.

Another object of the invention is to provide a process for the preparation of higher oxo aldehydes or the corresponding alcohols from olefins or olefin mixtures which is additionally distinguished by high space-time yields and offers more room for maneuver to control product properties.

Briefly, these objects and other objects of the present invention as hereinafter will become more readily apparent can be attained by a process for hydroformylating olefins to give alcohols and/or aldehydes in at least one hydroformylation stage, each of which comprises:

a) hydroformylating olefins having a carbon atom content of 6 to 24 carbon atoms in the presence of a cobalt- or rhodium catalyst in a reactor to the point of conversion of olefin reactant to product of 20 to 98%;

b) removing the catalyst from the resulting liquid discharged from the reactor;

c) separating the resulting liquid hydroformylation mixture into a low-boiler fraction comprising olefins and paraffins, and a bottoms fraction comprising aldehydes and/or alcohols; and d) reacting the olefins present in the low-boiler fraction in additional process stages comprising steps a, b and c and combining the bottoms fractions of process steps c) of all process stages.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The process variants of the invention can in each case be conducted discontinuously or continuously, preferably in two hydroformylation processes or stages. For a continuous procedure various process variants are possible, which are shown by way of example as two-stage processes in FIGS. 1 to 3. These embodiments are referred to below as variants 1, 2 and 3. It should be emphasized that the procedures described herein are of course also applicable for processes with more than two process stages.

The crude aldehyde obtained by means of the process of the invention which, in addition to the process products aldehyde and alcohol, also comprises formates, condensation products and other high-boiling components, is worked-up either by distillation to isolate the aldehyde, or the crude product is first hydrogenated and then distilled to isolate the alcohols.

The process according to the invention is preferably conducted such that the liquid reactor discharge of hydroformylation step a) is a homogeneous liquid phase. The cobalt or rhodium catalysts are preferably employed such that they are dissolved homogeneously in the liquid reactor discharge of hydroformylation step (a) of the process.

The unreacted olefins are separated from the aldehydes formed following removal of excess synthesis gas and catalyst in one or more separation steps or distillation steps. The hydroformylation products from the first process stage are therefore not again subjected in one or more further stages to the conditions of a hydroformylation reaction which favor consecutive reactions.

Variant 1

Figure 1:
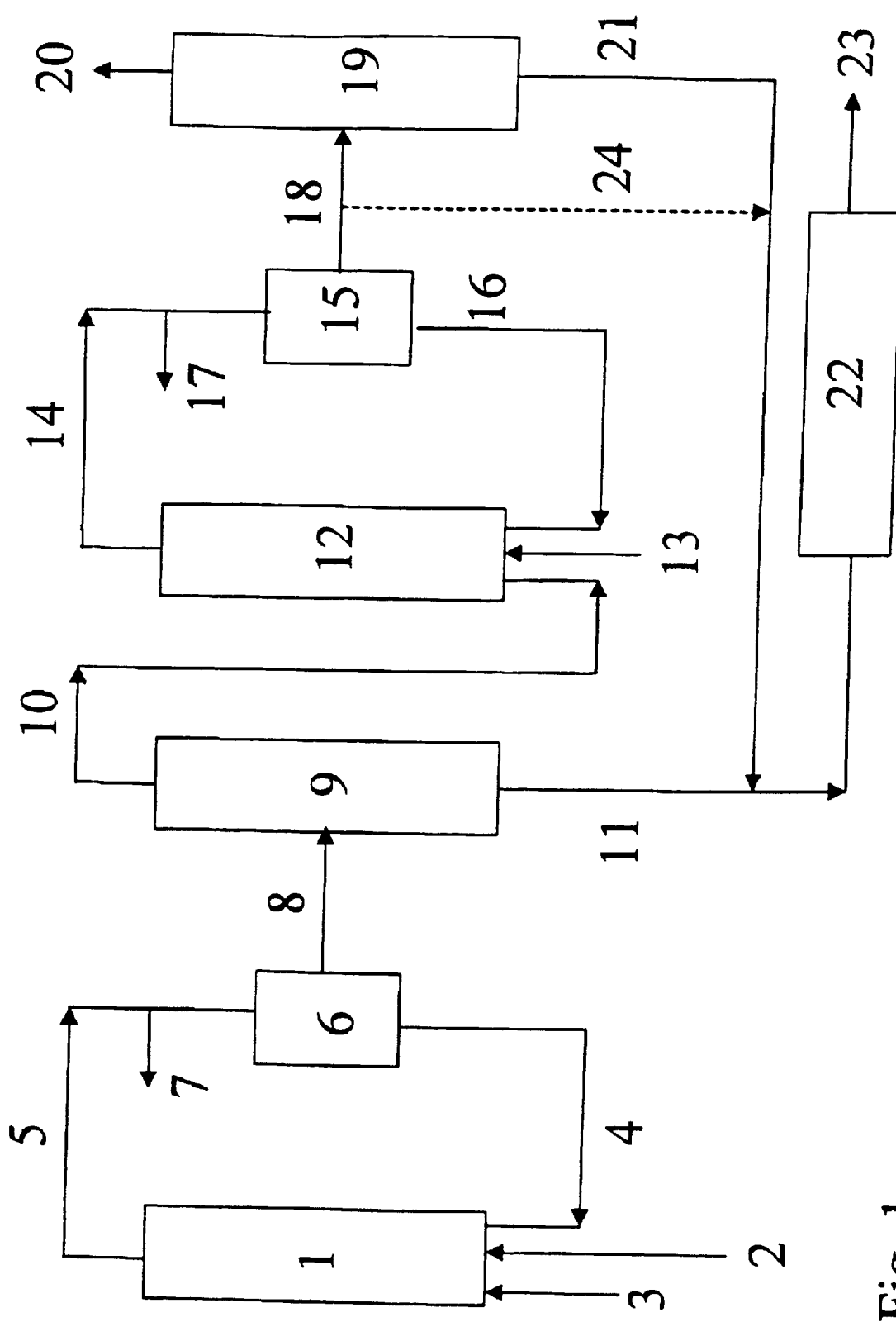
FIG. 1 is a schematic diagram of the process of Variant 1 of the present multistage method of hydroformylating olefins to alcohol/aldehyde product.

The process of Variant 1 is shown as a block diagram in FIG. 1. The olefin mixture 3, the synthesis gas 2 (carbon monoxide and hydrogen), and catalyst solution or the precursors of the catalyst 4 are fed to the first hydroformylation reactor 1. The resulting hydroformylation mixture 5 is decompressed, the decompression gas 7 (unconsumed synthesis gas) is drawn off and the decompressed hydroformylation mixture is freed from the catalyst 4 in the first catalyst removal section 6, the catalyst, optionally after removal of a small partial stream and after topping-up with fresh catalyst, being returned to the first hydroformylation reactor 1. The term catalyst here also refers to precursors of catalysts, e.g. cobalt (II) salt solutions. The hydroformylation mixture 8 freed from the catalyst is separated in the distillation column 9 into low-boiling components 10, which consist predominantly of unreacted olefins, and crude aldehyde 11. The low-boiling components 10, synthesis gas 13 and catalyst solution 16 are introduced into the second hydroformylation reactor 12. The hydroformylation step of the second process stage can be conducted using the same catalyst system (both metal and ligand or their respective concentration) or using another catalyst system of the first stage. The hydroformylation mixture 14 from the second hydroformylation reactor 12 is again decompressed, and the decompression gas 17 is drawn-off. The decompressed hydroformylation mixture 14 is freed from the catalyst 16 in the second catalyst removal section 15, the catalyst in turn, optionally after removal of a small partial stream and after topping-up with fresh catalyst, being returned to the second hydroformylation reactor 12. The catalyst-free hydroformylation mixture 18 can be separated in column 19 into low-boiling components 20, which consist predominantly of saturated hydrocarbons, and crude aldehyde 21. In some instances, some of the low-boiling components 20 may be returned to the reactor 12. (Line not shown in FIG. 1).

A further embodiment of this process variant consists of passing the hydroformylation mixture 18, which is freed from catalyst, together with the crude aldehyde 11 to hydrogenation reactor 22 without distillation in column 19 (line 24). The crude aldehydes 11 and 21 or 11 and 24 are hydrogenated in the hydrogenation reactor 22 with hydrogen to give the crude alcohol 23, which can optionally be worked-up in a distillation unit (not shown) to give pure alcohol. If the aldehyde is the actual target product, the hydrogenation unit 22 is bypassed and, where necessary, the crude aldehyde (11 and 21 or 11 and 24) is worked-up in a distillation (not shown) to give pure aldehyde.

In this variant of the invention, each process stage has a hydroformylation step a), a catalyst removal step b) and a distillation step c), with the proviso that the catalyst separated in b) is returned, directly or after work-up, to the hydroformylation step a) of the respective process stage.

Optionally, this process variant can also be conducted such that the last process stage does not have a distillation step c).

Variant 2

Figure 2:
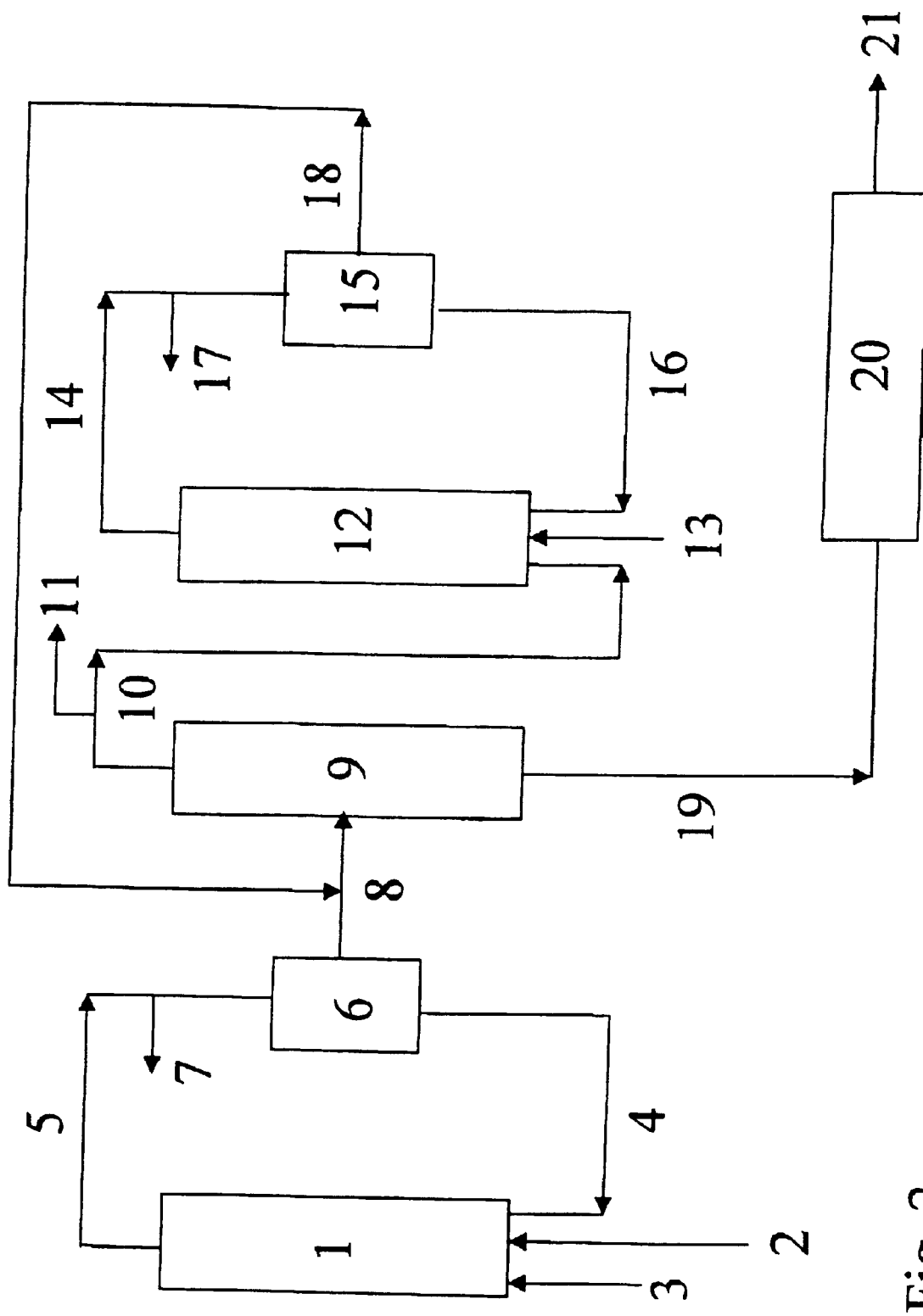
FIG. 2 is a schematic diagram of the process of Variant 2 of the present multistage method of hydroformylating olefins to alcohol/aldehyde product.

The block diagram of another process variant of the invention is shown in FIG. 2. The olefin mixture 3, the synthesis gas 2 (carbon monoxide and hydrogen), and catalyst 4 or its precursor are fed to the first hydroformylation reactor 1. The resulting hydroformylation mixture 5 is decompressed, the decompression gas 7 (unconsumed synthesis gas) is drawn-off and the decompressed hydroformylation mixture is freed from the catalyst 4 in the first catalyst removal section 6, the catalyst, optionally after removal of a small partial stream and after topping-up with fresh catalyst, being returned to the first hydroformylation reactor 1. The hydroformylation mixture 8 freed from the catalyst is passed to distillation unit 9. There, together with the catalyst-free hydroformylation mixture 18 from the second hydroformylation reactor 12, the hydroformylation mixture is separated into a low-boiler fraction 10, which comprises the unreacted olefins and inert paraffins, and crude aldehyde 19. The low-boiling components 10, after removal of a partial stream 11 in which saturated hydrocarbons (paraffins) and other nonolefinic compounds are removed, are passed together with synthesis gas 13 and catalyst 16 to the second hydroformylation reactor 12. The resulting hydroformylation mixture 14 is decompressed, the decompression gas 17 is drawn-off, and the decompressed hydroformylation mixture is freed from catalyst 16 in the second catalyst removal section 15, the catalyst, optionally after removal of a small partial stream and after topping-up with fresh catalyst, being returned to the second hydroformylation reactor 12. The catalyst-free second hydroformylation mixture 18 is fed with the hydroformylation mixture 8 from the first stage, as already mentioned, to the distillation column 9. The crude aldehyde 19 can be hydrogenated in the hydrogenation unit 20 with hydrogen 10 to give the crude alcohol 21. This alcohol can in turn be worked-up in a distillation apparatus (not shown) to give pure alcohol. If an aldehyde is the target product, the crude aldehyde 19 bypasses the hydrogenation unit, and is worked-up in a distillation unit (not shown) to give pure aldehyde.

The term catalyst here may also mean precursors of catalysts, e.g. cobalt (II) salt solutions. The second and each further process stage can be conducted using the same catalyst system (both metal and ligand or their respective concentration) or using a system different to the first stage.

Instead of being removed via the partial stream 11, the saturated hydrocarbons can also be removed by working-up a partial stream of the hydroformylation product 18 freed from the catalyst (not shown). On an industrial scale, this can be conducted, for example, by separating this partial stream by distillation into low-boiling components, which are removed, and aldehydes, which are returned to the catalyst-free hydroformylation mixture 18 or the crude aldehyde 19.

This variant of the invention has, for each process stage, a hydroformylation step a) and a catalyst removal step b), the combined liquid hydroformylation mixtures being separated in a common distillation step c) into a low-boiler fraction and bottoms fraction, with the proviso that the catalyst separated in steps b) is returned, directly or after work-up, to the hydroformylation step a) of the respective process stage.

Variant 3

Figure 3:
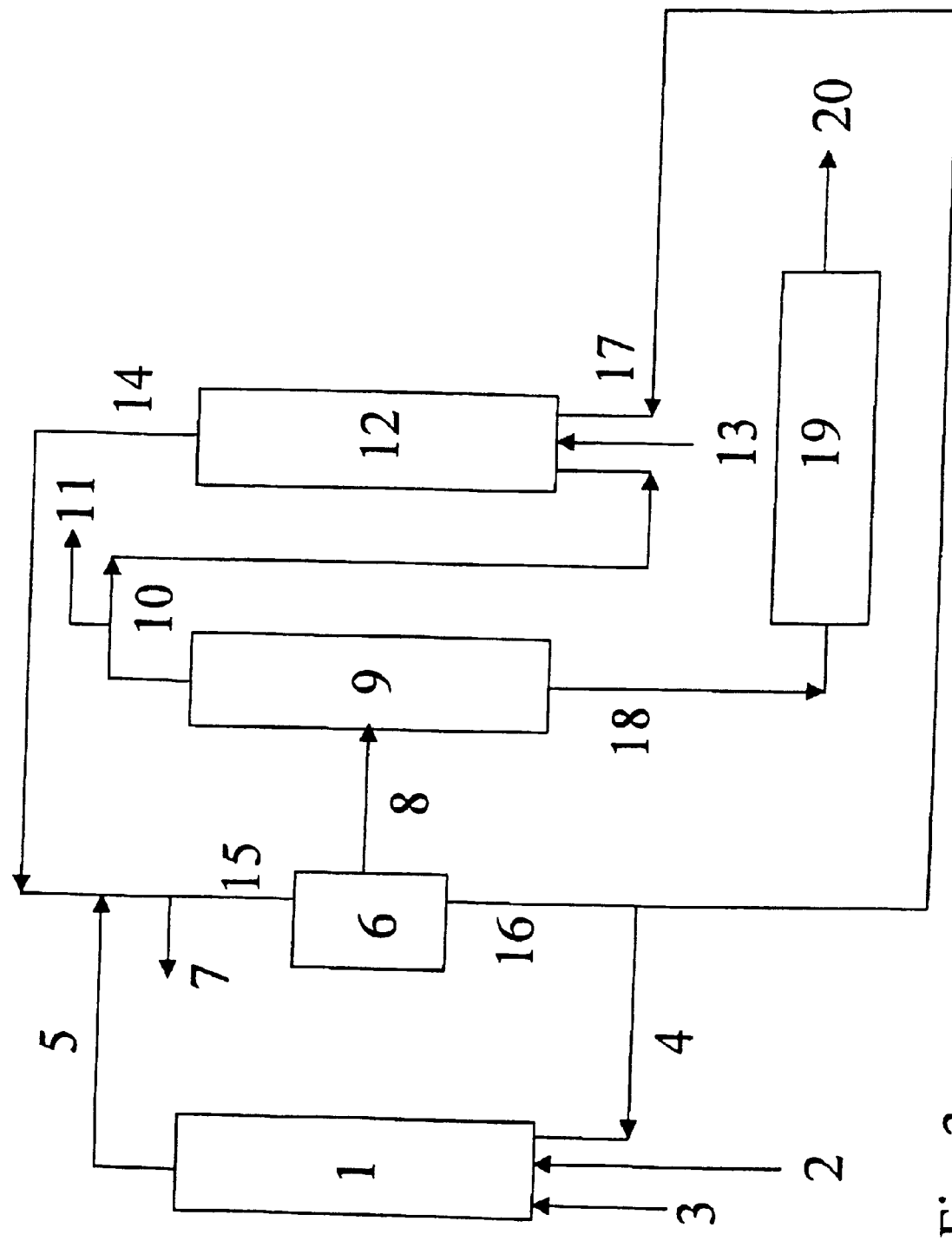
FIG. 3 is a schematic diagram of the process of Variant 3 of the present multistage method of hydroformylating olefins to alcohol/aldehyde product.

Still another variant of the process of the invention is shown in FIG. 3. The olefin mixture 3, the synthesis gas 2 (carbon monoxide and hydrogen), and catalyst solution or precursor thereof 4 are fed to the first hydroformylation reactor 1. The resulting hydroformylation mixture 5 is decompressed together with the hydroformylation mixture 14 from the second hydroformylation reactor 12 as combined hydroformylation discharge material 15, and the decompression gas 7 (unconsumed synthesis gas) is drawn-off. The combined hydroformylation discharge material is freed from catalyst 16 in the catalyst removal section 6, giving a mixture 8 comprising the formed aldehydes, alcohols and unreacted olefins. The catalyst 16, optionally after removal of a partial amount of and topping-up with fresh catalyst, is subdivided into the two partial streams 4 and 17. Partial stream 4 is returned to the first hydroformylation reactor 1 and partial stream 17 is returned to the second hydroformylation reactor 12. The catalyst-free hydroformylation discharge material 8 is separated in the distillation column 9 into the low-boiling components 10 and the crude aldehyde 18. The low-boiler fraction 10, which comprises the unreacted olefins, optionally after removal of a partial amount 11 (to remove saturated hydrocarbons or other nonolefinic compounds), is fed together with synthesis gas 13 and catalyst 17 to the second hydroformylation reactor 12. The crude aldehyde 18 can be hydrogenated in the hydrogenation unit 19 with hydrogen to give the crude alcohol 20. The latter can in turn be worked-up in a distillation (not shown) to give pure alcohol. If the aldehyde is the target product, the hydrogenation unit 19 is bypassed and the crude aldehyde 18 is worked-up by distillation to give pure aldehyde (not shown).

In the case of variant 3 too, it is possible to remove saturated hydrocarbons via a separate work-up of a partial stream of the hydroformylation mixture 14, for example, by distillative removal of the low-boiling components.

This variant of the process of the invention is notable for the fact that the combined reactor discharge material of all hydroformylation steps a) pass through only a catalyst removal step b) and a distillation step c), with the proviso that the catalyst separated in the process steps b) is divided, directly or after work-up, and returned to the hydroformylation steps a) of the individual process stages.

In this variant too, catalyst also encompasses precursors of catalysts, e.g. cobalt (II) salt solutions.

In this process variant, the same catalyst, i.e. cobalt or rhodium as active catalyst metal, must be used in all hydroformylation steps or process stages. It is, however, possible to use different catalyst concentrations in different process stages or hydroformylation steps thereof.

In the process of the invention it is possible to return all or some of the excess synthesis gas, which is separated, to the process. A particularly interesting possibility arises when the hydroformylation reactors are operated at different pressures. The off-gas from reactors which are operated at higher pressure than others can be separated at a pressure above the operating pressure of the other reactors, meaning that it can be used in the other reactors without compression.

The common feature of the invention or of variants 1 to 3 is the hydroformylation of olefins or olefin mixtures in a plurality, preferably in two, stages, where in the first stage predominantly the more reactive olefins are converted and in the further stages predominantly the less reactive olefins are converted.

Another essential feature of the invention is the removal of unreacted olefins present in the low-boiling components from the hydroformylation product of the first stage discharged as a liquid, after removal of the catalyst, preferably by distillation. The essential differences between the individual variants consist in the complexity of working-up the reaction discharge material. By virtue of the separately operating catalyst cycles, variant 1 permits the use of different catalysts, of different catalyst concentrations or of different ligand systems in the reactors. In variant 1, these separate distillation operations guarantee the best removal of paraffins produced in the process. It is, however, possible to save at least one of the distillation material and to separate the discharge material from the various hydroformylation reactors in just one distillation step (variant 2). A further reduction in the required apparatus is achieved by combining the catalyst cycles (variant 3). Although different catalysts can no longer be used in the process stages, the concentration of the catalyst in the reactors can still be adjusted by means of the splitting ratio (partial streams 4 and 17 in the case of a two-stage process according to FIG. 3) of the recycled catalyst. Also, the reaction conditions such as pressure, temperature, and the like can still be chosen freely independently of one another for each hydroformylation step.

The reactors in which the hydroformylation is conducted can be identical or different in all process stages. Examples of types of reactors which can be used are bubble columns, loop reactors, jet-nozzle reactors, stirred reactors and tubular reactors, some of which may be cascaded and/or provided with internals.

Description of the Starting Materials, Process Conditions and Products

The starting materials for the process are olefins or mixtures of olefins having 6 to 24 carbon atoms, advantageously having 6 to 20 carbon atoms, in particular having 8 to 20 carbon atoms, and having terminal or internal C-C double bonds. The mixtures can consist of olefins of identical, similar (±2) or significantly different (>±2) carbon number. Examples of olefins, which can be used as starting material either in pure form, in an isomer mixture or in a mixture with further olefins of different carbon number, which may be mentioned include 1-, 2- or 3-hexene, 1-heptene, linear heptenes having an internal double bond (2-heptene, 3-heptene etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctenes, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond, mixtures of linear hexadecenes. Suitable starting materials also include, inter alia, the mixture of isomeric hexenes (dipropene) produced during the dimerization of propene, the mixture of isomeric octenes (dibutene) produced during the dimerization of butenes, the mixture of isomeric nonenes (tripropene) produced during the trimerization of propene, the mixture of isomeric dodecenes (tetrapropene or tributene) produced during the tetramerization of propene or the trimerization of butenes, the hexadecene mixture (tetrabutene) produced during the tetramerization of butenes, and olefin mixtures prepared by cooligomerization of olefins of different carbon number, preferably 2 to 4, optionally after distillative separation into fractions of identical or similar (±2) carbon number. It is also possible to use olefins or olefin mixtures which have been prepared by Fischer-Tropsch synthesis. Moreover, olefins which have been prepared by olefin metathesis or by other industrial processes can be used. Preferred starting materials are mixtures of isomeric octenes, nonenes, dodecenes or hexadecenes, i.e. oligomers of lower olefins, such as n-butenes, isobutene or propene. Other likewise highly suitable starting materials are oligomers of $C_5$-olefins.

For the oligomerization of butenes to mixtures comprising essentially $C_8$-olefins there are in principle three process variants. The oligomerization over acid catalysts has been known for a long time, zeolites or phosphoric acid on supports, for example, being used in industry. This process produces isomer mixtures of branched olefins which are essentially dimethylhexenes (WO 92/13818). A process which is likewise used throughout the world is oligomerization using soluble Ni complexes, known as DIMERSOL process (B. CORNILS, W. A. HERRMANN, *"Applied Homogeneous Catalysis with Organometallic Compounds"*; Vol. 1&2, VCH, Weinheim, New York 1996). The third process variant is oligomerization over nickel fixed-bed catalysts. This process has gained access into the literature as the OCTOL process (Hydrocarbon Process., Int. Ed. (1986), 65 (2. Sect. 1) page 31–33).

For the preparation of the invention of a $C_9$ alcohol mixture which is particularly suitable for the preparation of plasticizers, preference is given to a $C_8$-olefin mixture which has been obtained from linear butenes by the OCTOL process.

In the synthesis gas used for the hydroformylation carbon monoxide and hydrogen are generally present in the molar ratio of 1:4 to 4:1 and preferably in an approximately stoichiometric ratio.

The process of the invention is conducted with a cobalt or rhodium catalyst, and with or without a complex-stabilizing additive, such as an organic phosphine or phosphite. In all of the hydroformylation steps of the process it is possible to use either rhodium catalysts or cobalt catalysts. It is also possible to use a cobalt catalyst (alternatively: rhodium catalyst) in the hydroformylation step a) in the first process stage, and to use rhodium catalysts (alternatively: cobalt catalyst) in the hydroformylation steps of the further process stages. An advantage of the process of the invention is that different catalysts can be used in the individual stages, meaning that in cases of more than two process stages it is also possible to use different catalysts, e.g. cobalt/rhodium/cobalt.

The choice of catalyst and of reaction conditions (concentration of the catalyst, temperature, pressure, residence time) depends, inter alia, on the number of carbon atoms and the composition of the starting olefins. If a high proportion of terminally hydroformylated olefin is a criterion for high product quality, then, for example in the case of the dimerization mixture of n-butenes known as di-n-butene, very good product quality is achieved coupled with satisfactory yield if, in the case of a two-stage process, unmodified cobalt catalysts are used in both stages. If an unmodified cobalt catalyst is used in the first stage and an unmodified rhodium catalyst is used in the subsequent stages, then the yield improves, while the product quality is somewhat diminished. A further improvement in yield and a reduction in product quality arise if unmodified rhodium catalysts are used in all stages. If a low proportion of terminally hydroformylated olefin is a criterion for high product quality, then, for example, in the case of the dimerization mixture of n-butenes known as di-n-butene, good product quality is achieved coupled with a very high yield if, in the case of a two-stage process, unmodified rhodium catalysts are used in both stages. If ligand-modified catalysts are used, in particular if rhodium and phosphorus ligands are used, there is also further scope for influencing the proportion of terminally or nonterminally hydroformylated olefin via the choice of ligand. For a given starting olefin, the optimum number of process stages, and in the individual hydroformylation steps, the optimal catalysts can be determined without difficulty by exploratory experiments. The catalyst concentrations in the individual stages can be identical or different.

The temperatures and the pressures in the hydroformylation steps of the various process stages can vary within wide limits, depending on the catalyst and olefin mixtures. Since in the first stage the more reactive olefins react in preference, in the hydroformylation steps of the further stages more energetic reaction conditions with regard to temperature, amount of catalyst, residence time are advantageously used.

The optimal conditions can vary from case to case depending on the objective. For example, the space-time yield achieved overall, the increase in the selectivity or the desired product properties may be aspects of the process subject to optimization criteria. As a rule, the composition of the starting olefin and the choice of catalyst systems and/or reaction conditions determine which of the possible embodiments of the process of the invention is the economically optimal.

In the process of the invention, olefin conversions in the hydroformylation steps of the individual process stages range from 20 to 98%, in particular from 40 to 80%, particularly preferably 50 to 75% (in each case single pass).

In the hydroformylation steps a) of the further process stages which follow the first process stage, the olefins can in each case be reacted to a conversion of at least 50%, preferably 55 to 98%.

It is an advantage of the process of the invention that different reaction conditions can be set in the hydroformylation reactors. This allows the hydroformylation conditions to be matched to the reactivity of the olefin mixture introduced. To minimize secondary products and byproducts it is, for example, it makes sense to react the reactive olefins under the mildest conditions possible, so that virtually no secondary products and byproducts form therein. Then, in the following reactor, the olefin mixture which remains, which largely consists of the unreactive olefins, is hydroformylated under, where necessary, more severe conditions. It is therefore possible to influence the isomer distribution of the aldehydes formed by the varying reaction conditions in the reactors.

Rhodium- and cobalt-catalyzed hydroformylation processes differ mostly by virtue of their operating parameters. However, the main difference is in the fundamentally different catalyst removal and recycle. The two processes are described separately below.

Cobalt-catalyzed Hydroformylation Process

In the cobalt-catalyzed hydroformylation of olefins it is possible to use unmodified and/or modified catalysts which may be identical or different for each process stage. The hydroformylation process in each of the cobalt-catalyzed process stages can be conducted by a one-stage process described in DE 196 54 340. According to this process, the starting materials, the cobalt salt solution, the organic phase and the synthesis gas are simultaneously introduced into the reactor concurrently from below, preferably using a mixing nozzle.

The cobalt compounds used are preferably cobalt salts, such as formates, acetates or salts of carboxylic acids which are water-soluble. Cobalt acetate has proven particularly successful. This compound is used as an aqueous solution with a cobalt content ranging from 0.5 to 3% by weight, preferably from 1.0 to 2.0% by weight, calculated as metal.

The organic phase comprises the olefin to be hydroformylated and optionally additionally an aldehyde and/or alcohol, the aldehyde or alcohol preferably being the reaction products formed during the hydroformylation.

In the cobalt-catalyzed process, particular importance is attached to the metered addition of the starting materials into the reactor. The metering device must ensure good phase mixing and the production of the greatest possible phase exchange area. In the case of cobalt-catalyzed hydroformylation, it is therefore advantageous to divide the reactor space of the hydroformylation reactors by incorporating a small number of perforated sheets (minimum number=1) arranged perpendicularly to the flow direction of the reactant and product stream. As a result of the cascade of materials in the reactor, back-mixing is considerably reduced compared with the conditions in the simple bubble column and the flow behavior approximates that of a tubular reactor. This process engineering measures result in both the yield and the selectivity of the hydroformylation being improved.

If, according to the invention, hydroformylation steps with cobalt catalyst are used, then the steps are operated at temperatures ranging from 100 to 250° C. and under pressures ranging from 100 to 400 bar. Temperatures ranging from 140 to 210° C. and synthesis gas pressures ranging from 200 to 300 bar have proven particularly successful. The volume ratio of the carbon monoxide to the hydrogen in the synthesis gas generally ranges from 2:1 to 1:2, in particular the volume ratio of 1:1. The synthesis gas is advantageously used in excess, for example in up to three times the stoichiometric amount.

The hydroformylation of olefins is conducted under cobalt catalysis in the first process stage, in which the more reactive olefins are converted, at temperatures ranging from 140 to 195° C., preferably at 160 to 185° C. Olefin conversions from 20 to 90%, preferably from 50 to 80%, are desired for this process stage.

After leaving the reactor of the first process stage or of the first hydroformylation step, the product discharge material is decompressed to 10 to 15 bar and passed to the decobalting (catalyst removal, 6 in FIG. 1). In the decobalting step, the product discharge (organic phase) is freed from cobalt carbonyl complexes in the presence of "process water" using air or oxygen at temperatures ranging from 130 to 190° C. The decobalting processes are well known and described in the literature in detail, such as e.g. by J. FALBE, in "New Syntheses with Carbon Monoxide", Springer Verlag (1980), Berlin, Heidelberg, New York, page 158 et seq.

The decobalting is preferably conducted in a pressurized container filled with dumped packing, such as, for example, Raschig rings in which the highest possible phase exchange area is generated. The cobalt free organic product phase is separated from the aqueous phase in a downstream separation container. The aqueous phase, the "process water", which contains the back-extracted cobalt recovered from the organic phase in the form of cobalt acetate/formate, is, wholly or following removal of a small fraction, returned to the oxo reactor of the respective process stage and preferably used as starting material for the in situ preparation of the cobalt catalyst complexes.

Precarbonylation, catalyst extraction and the actual hydroformylation are preferably conducted in one reactor as disclosed in DE 196 54 340. It is also possible to separate these process stages from one another in terms of apparatus.

The organic reactor discharge, which contains the unreacted olefins, aldehydes, alcohols, formic esters and high-boiling components is, after the hydroformylation step and the catalyst removal, passed to a distillation step. Here, the reactor discharge material freed from the cobalt catalyst and excess synthesis gas is separated by distillation into the crude aldehydes/alcohols (bottoms fraction) and a low-boiler fraction which, depending on the process variant and conditions of the hydroformylation step, consists predominantly of the unreacted, less reactive olefins and/or paraffins produced by hydrogenation of the olefins.

The unreacted olefins freed from the products of value in the distillation step are then passed to the hydroformylation step of the next process stage.

According to the process of the invention, the cobalt-catalyzed hydroformylation is conducted in the further process stages following the first stage or hydroformylation steps at temperatures ranging from 160 to 220° C., preferably from 175 to 195° C. Here, olefin conversions of at least 50%, preferably from 50 to 95%, preferably from 55 to 98% are targeted.

The multistage process of the invention offers the possibility of bringing the olefin conversion in the first stage to the targeted value by adapting the reaction conditions, for example, by choosing low cobalt concentrations. In the following stages, where the more slowly reacting olefins are converted, the reaction conditions can then be intensified, for example, by increasing the catalyst concentration.

The process stages of the invention using cobalt catalyst are particularly suitable for the hydroformylation of mixtures of isomeric olefins prepared by oligomerization of propene and butenes. Typical oligomerization products which are preferably used as raw material base for the hydroformylation of the present process include di-, tri- and tetrapropene, and di-, tri-, and tetrabutene.

Rhodium-catalyzed Hydroformylation

In rhodium-catalyzed hydroformylation processes it is possible to employ modified and/or unmodified catalysts which may be identical or different for each rhodium catalyzed hydroformylation step. These rhodium catalysts can be introduced into the process in the form of their active complexes, although in industry it is usually simpler to generate the active catalysts in situ from stable, readily storable rhodium compounds. Suitable rhodium compounds for this purpose are, for example, include rhodium(II) and rhodium(III) salts, such as rhodium(III) chloride, rhodium (III) nitrate, rhodium(III) sulfate, potassium rhodium sulfate, rhodium(II) and rhodium(III) carboxylate, rhodium(II) and rhodium(III) acetate, rhodium(II) octanoate, rhodium(II) nonanoate, rhodium(III) oxide, salts of rhodic(III) acid, trisammonium hexachloro-rhodate(III). Also suitable are rhodium complexes, such as acetylacetonatodicarbonylrhodium, acetylacetonato-bisethylenerhodium(I). Rhodium acetate, rhodium octanoate and rhodium nonanoate are particularly suitable.

In general, approximately 1 to 500 and, preferably, 3 to 50 mol of ligand are added per mole of rhodium. Fresh ligand can be added to the reaction at any time in order to keep the concentration of free ligand constant.

The concentration of the rhodium in the hydroformylation reactor ranges from 1 ppm to 500 ppm, preferably from 5 ppm to 200 ppm.

The choice of ligands added is not limited in the process according to the invention, but depends on the olefin used and on the desired products. Preferred ligands are ligands which contain nitrogen, phosphorus, arsenic or antimony atoms, particular preference being given to phosphorus ligands. The ligands can be monodentate or polydentate, and in the case of chiral ligands either the racemate or an enantiomer or diastereomer can be used. Suitable phosphorus ligands include, in particular, phosphines, phosphine oxides, phosphites, phosphonites and phosphinites. Examples of phosphines are triphenyl-phosphine, tris(p-tolyl)phosphine, tris(m-tolyl)phosphine, tris(o-tolyl) phosphine, tris(p-methoxy-phenyl)phosphine, tris(p-fluorophenyl)phosphine,tris-(p-chlorophenyl)phosphine,tris (p-dimethylaminophenyl)phosphine, ethyldiphenylphosphine, propyldiphenylphosphine, t-butyldiphenylphosphine, n-butyldiphenylphosphine, n-hexyldiphenylphosphine, c-hexyldiphenylphosphine, dicyclohexylphenylphosphine, tricyclohexylphosphine, tricyclopentylphosphine, triethylphosphine, tri(1-naphthyl) phosphine, tri-2-furylphosphine, tribenzylphosphine, benzyldiphenylphosphine, tri-n-butylphosphine, tri-i-butylphosphine, tri-t-butylphosphine, bis(2-methoxyphenyl) phosphine, neomenthyldiphenylphosphine, the alkali metal, alkaline earth metal, ammonium or other salts of sulfonated triphenylphosphines, such as tris(m-sulfonylphenyl) phosphine, (m-sulfonylphenyl)diphenylphosphine, 1,2-bis (dicyclohexylphosphino)ethane, bis (dicyclohexylphosphino)methane, 1,2-bis (diethylphosphino)ethane, 1,2-bis(2,5-diethylphospholano) benzene [Et-DUPHOS], 1,2-bis(2,5-diethylphospholano) ethane [Et-BPE], 1,2 bis(dimethylphosphino)ethane, bis (dimethylphosphino)-methane, 1,2-bis(2,5-dimethylphospholano)benzene [Me-DUPHOS], 1,2-bis(2,5-dimethylphospholano)ethane[Me-BPE], 1,2-bis (diphenylphosphino)benzene, 2,3-bis (diphenylphosphino) bicyclo[2.2.1]hept-5-ene [NORPHOS], 2,2'-bis (diphenylphosphino)-1,1'-binaphthyl [BINAP], 2,2'-bis (diphenylphosphino)-1,1'-biphenyl [BISBI], 2,3 bis (diphenylphosphino)butane, 1,4-bisdiphenyl phosphino) butane, 1,2-bis(diphenylphosphino)ethane, bis(2-diphenylphosphinoethyl)phenylphosphine, 1,1'-bis (diphenylphosphino)ferrocene, bis(diphenylphosphino) methane, 1,2-bis(diphenylphosphino)propane, 2,2'-bis(di-p-tolylphosphino)-1,1'-binaphthyl, 0-isopropylidene-2,3-dihydroxy-1,4-bis(diphenylphosphino)butane[DIOP], 2-(diphenylphosphino)-2'-methoxy-1,1'-binaphthyl, 1-(2-diphenylphosphino-1-naphthyl)isoquinoline, 1,1,1-tris (diphenylphosphino)ethene, tris(hydroxypropyl)phosphine.

A particularly preferred phosphine used is triphenylphosphine.

Suitable examples of phosphates include trimethyl phosphite, triethyl phosphite, tri-n-propyl phosphite, triisopropyl phosphite, tri-n-butyl phosphite, triisobutyl phosphite, tri-t-butyl phosphite, tris(2-ethylhexyl)phosphite, triphenylphosphite, tris(2,4-di-t-butylphenyl)phosphite, tris (2-t-buyl-4-methoxyphenyl)phosphite, tris(2-t-butyl-4-methylphenyl)phosphite, tris(p-cresyl)phosphite. Also included are sterically hindered phosphite ligands, as described inter alia in EP 155 508, U.S. Pat. Nos. 4,668,651, 4,748,261, 4,769,498, 4,774,361, 4,835,299, 4,885,401, 5,059,710, 5,113,022, 5,179,055, 5,260,491, 5,264,616, 5,288,918, 5,360,938, EP 472 071, EP 518 241 and WO 97/20795. Preferred phosphites are substituted triphenyl phosphites having in each case 1 or 2 isopropyl and/or tert-butyl groups on the phenyl rings, preferably in the ortho-position relative to the phosphite ester group.

Suitable examples of phosphonites include methyldiethoxyphosphine, phenyldimethoxyphosphine, phenyldiphenoxyphosphine, 6-phenoxy-6H-dibenz[c,e][1, 2]oxaphosphorine and derivatives thereof, in which the hydrogen atoms are wholly or partially replaced by alkyl or aryl radicals or halogen atoms, and ligands which are described in patents WO 98/43935, JP 09-268152 and DE 198 10 794 and in the German patent applications DE 199 54 721 and DE 199 54 510.

Common phosphonite ligands are described inter alia in U.S. Pat. No. 5,710,344, WO 95/06627, U.S. Pat. No. 5,360,938, JP 07082281. Suitable examples thereof include diphenyl(phenoxy)phosphine and derivatives thereof in which the hydrogen atoms are wholly or partially replaced by alkyl or aryl radicals or halogen atoms, diphenyl (methoxy)phosphine, diphenyl(ethoxy)phosphine, and the like.

Rhodium-catalyzed hydroformylation reactions are generally conducted at pressures ranging from 1 to 300 bar, preferably at pressures from 15 to 270 bar. The pressure to which the reaction medium is subjected depends on the structure of the feed olefins, the rhodium catalyst employed and the desired effect. Thus, for example, (α-olefins can be converted to the corresponding aldehydes at pressures below 64 bar with high space-time yields. By contrast, in the case of olefins with internal double bonds, in particular in the case of branched olefins, higher pressures are expedient.

The temperatures for rhodium-catalyzed hydroformylation reactions generally range from 40° C. to 180° C., preferably 60° C. to 135° C. Temperatures above 100° C. afford the technical advantage that the waste heat from the reaction can be utilized to generate steam.

Following the hydroformylation, most of the synthesis gas is removed by relieving the pressure. The catalyst is removed from the liquid reaction discharged by distillation (catalyst removal e.g. 6 and 15 in FIG. 1). The catalyst and optionally added ligands, stabilizers, and the like remain in/as distillation residue. It is therefore advantageous to use a high-boiling (higher boiling than products and starting materials) inert solvent in which the catalyst dissolves. The catalyst dissolved in the high-boiling solvent can then be returned directly to the reaction. It is particularly advantageous to use the high-boiling byproducts formed in the process as high-boiling solvent. Other suitable solvents are high-boiling esters, such as 2,2,4-trimethylpentanediol 1,3-monoisobutyrate, which is available commercially as Texanol.

In order to effect catalyst removal by a distillative procedure in industrial processing, a variety of procedures can be used. Preference is given to removing the catalyst solution by falling-film, short-path or thin-film evaporators or combinations of these apparatuses. The advantage of such a combination can, for example, be the fact that still dissolved synthesis gas and some of the products and the still present starting olefins can be separated in a first step (for example in a falling-film evaporator) in order then, in a second step (for example in a thin-film evaporator), to undertake the final removal of the catalyst.

Since the hydroformylation of olefins is an exothermic reaction, the heat produced has to be eliminated from the reactors in order to limit the temperature in the reactor. Temperatures which are too high generally bring about an increased formation of byproducts and deactivation of the catalyst. Often, it is desirable to employ as much of an isothermic procedure as possible, because the reaction temperature can have a direct influence on the product composition (e.g. the n/i ratio).

The dissipation of heat is possible via various technical arrangements, for example, via the reactor wall, integrated condenser, or the like. Industrially, it is advantageous to keep the expenditure for the dissipation of heat low. However, if olefin mixtures are used, the varying reaction rates can lead to the generation of considerable heat as a result of the exothermicity of the reaction, in particular in the first stage, since here the readily oxidizable components preferably react. The process of the invention then offers the possibility of keeping the evolution of heat, predominantly in the first process stage, within limits which can be readily controlled in industry, by adapting the reaction conditions, for example, by employing low catalyst concentrations or by adding an inert solvent.

Work-up of the Catalyst-free Hydroformylation Mixtures

The materials discharged from the reactor are freed of catalyst and excess synthesis gas, as shown in FIGS. 1-3. The materials are separated, separately or together, into the crude aldehydes and a low-boiler fraction by distillation. Depending on the processing variant and process stage, the low-boiling components consist predominantly of unreacted olefins or paraffins formed by hydrogenation of the olefins. In addition to aldehydes and alcohols, the bottom product also comprises high-boiling byproducts, such as formates, acetals, saturated and unsaturated ethers, esters, carboxylic acids and condensation products. The hydroformylation discharge material freed from the catalyst can be separated into low-boiling components and crude aldehyde separately in one or more distillations (variant 1) or in a common distillation (variants 2 and 3). The distillation conditions depend on the boiling points of the components and thus primarily on the molecular weights of the olefins and aldehydes. Conditions are selected on the basis of reducing as much as possible the amounts of byproducts which are formed during the distillation. Since the byproducts originate mainly from reactions of the aldehydes at elevated temperatures, the distillation can be conducted under reduced pressure and in so doing the temperatures in the column can be kept low. It is, however, also possible to conduct the distillation at atmospheric pressure.

If the materials discharged from the hydroformylation reaction steps are distilled in separate distillation apparatus (variant 1), the low-boiling components of the first distillation are passed to the following process stage (generally: the low-boiling components from one stage to the next), and the low-boiling components from the last distillation are removed and optionally also in part returned to the previous hydroformylation stage. If the reaction materials discharged from different process stages are worked-up together (variants 2 and 3), it is expedient to remove some of the low-boiling components prior to entry into the last process stage or by working-up a partial stream of the material discharged from the last stage in order to keep the proportion of paraffins in the cycle to an acceptable level.

It is therefore possible to remove the paraffins, wholly or in part, from at least one low-boiler fraction.

Other aspects of the operational details of variants 1 to 3 is the removal of low-boiling components and also, in particular, the removal of paraffins from the process, as well as some process aspects. If removal of the catalyst and optionally also the distillation are conducted under reduced pressure, some of the low-boiling components and, also, undesirably, some of the product are removed from the process by the vacuum system. After condensation, this fraction may be discarded, or if the amount is sufficient it may be worth while to return the material (partially) to the process. Also, depending on the operating conditions, a fraction of low-boiling components and products is discharged by the excess synthesis gas which is separated, which components and products can be separated (for example by condensation) and optionally returned or worked-up.

The crude aldehydes, if they are the target product, are worked-up, separately according to stages or together, by distillation according to known methods to give the products.

Here, it is possible to work-up or separate, by distillation, the aldehydes of the combined bottom fractions from distillation step c) or, if distillation step c) of the last process stage is omitted, the combined bottom fractions and the material discharge d from the last catalyst removal step b) of the process.

If, on the other hand, the alcohols are the target products, the crude aldehydes are hydrogenated in the usual manner in the gaseous or liquid phase.

It is possible to hydrogenate either the combined bottom fractions from the distillation stages c) or, if the distillation step c) of the last process stage is omitted, the combined bottom fractions and the material discharged from the last catalyst removal step b) of the process.

For the hydrogenation, copper/nickel, copper/chromium, copper/chromium/nickel, zinc/chromium, nickel/molybdenum catalysts, for example, can be used. The catalysts can be support-free, or the active substances which promote hydrogenation or their precursors can be supported on materials, such as, for example, silicon dioxide or aluminum dioxide.

Preferred catalysts over which the hydroformylation mixtures are hydrogenated comprise in each case 0.3–15% by weight of copper and nickel and, as activators, 0.05–3.5% by weight of chromium and advantageously 0.01–1.6% by weight, preferably 0.02–1.2% by weight of an alkali metal component on a support material, preferably aluminum oxide or silicon dioxide. The stated amounts of materials refer to the as yet unreduced catalyst. The alkali metal component is optional.

The catalysts are advantageously used in a form in which they offer a low resistance to flow, e.g. in the form of granules, pellets or moldings, such as tablets, cylinders, extrudates or rings. They are expediently activated prior to use, e.g. by heating in a stream of hydrogen.

The hydrogenation, preferably a liquid-phase hydrogenation, is generally conducted under an overall pressure ranging from 5 to 30 bar, in particular from 15 to 25 bar. Hydrogenation in the gas phase can also be conducted at relatively low pressures, using correspondingly large gas volumes. If two or more hydrogenation reactors are employed, the overall pressures in each individual reactor can be identical or different within the stated pressure limits.

During hydrogenation in liquid or gaseous phase, the reaction temperatures generally range from 120 to 220° C., in particular from 140 to 180° C. Examples of such hydrogenation reactions are described in patent applications DE 198 42 369 and DE 198 42 370.

After the hydrogenation, the resulting reaction mixtures are worked-up by distillation. Where appropriate, olefins which have been separated can be returned to the hydroformylation stage.

Having now generally described this invention, a further understanding can be obtained by reference to certain specific Examples which are provided herein for purposes of illustration only and are not intended to be limiting unless otherwise specified.

EXAMPLES

Example 1

Conversion of Octene in Two Stages using Different Catalyst Ligands

A 100 g amount of 1-octene (>98%, GC) was converted in a one liter autoclave at 85° C. under a synthesis gas pressure of 20 bar. The rhodium catalyst was generated in situ from rhodium octanoate and ligand 1.

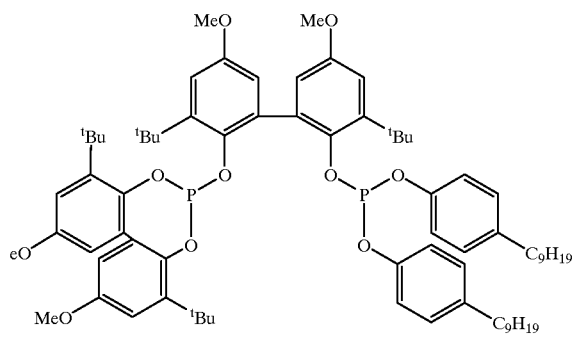

Ligand 1

200 ml of Texanol (2,2,4-trimethylpentanediol 1,3-monoisobutyrate) were added to the reaction as an inert high-boiling solvent. The rhodium concentration was adjusted to 40 ppm (based on the overall weight), and the phosphorus to rhodium ratio (P/Rh) was 20/1. The conversion of the olefin was monitored via the amount of absorbed synthesis gas. After a conversion of about 90% had been reached, virtually no more gas absorption was observed and the run was discontinued. According to GC analysis, the conversion was 91%, and the aldehyde formed consisted of 95% of nonanal. Analysis of the residual olefins produced only traces of 1-octene. The main constituents of the product were 2-octene, 3-octene and 4-octene, which had been formed by isomerization of the 1-octene.

The experiment was conducted six times, and the discharged olefin materials were combined and distilled. This processing gave 43 g of an octene mixture. The distilled olefin mixture was dissolved in 100 ml of Texanol, and hydroformylated again at 120° C. and a synthesis gas pressure of 50 bar in a 500 ml autoclave. The rhodium concentration was 40 ppm, and the ligand added was tris(2, 4-ditert-butylphenyl) phosphate (P/Rh 20/1). During this reaction, quantitative conversion of the olefin was achieved (GC).

The example shows that the catalyst system used in the first stage has a high n/iso selectivity, but only a low activity for the hydroformylation of octenes with an internal double bond, as are formed in the first stage by isomerization of the n-octene used (cf. P. W. N. M. van Leuwen et al., Organometallics 1996, 15, 835–847). However, these octenes containing internal double bonds can be reacted in a second stage under different conditions. Thus, on the one hand, the present process achieves high selectivity for the desired straight-chain nonanol and, on the other hand, achieves an improved overall yield of nonanol based on the feed material.

Example 2

Hydroformylation of di-n-butene in Two Stages using Different Catalysts

A 3 liter stirred autoclave was charged with about 1000 g of cobalt acetate-containing water (cobalt content about 1% by weight, calculated as metal). With stirring (1000 rpm), the mixture was placed under a synthesis gas pressure of 280 bar and the temperature was adjusted to 170° C. After 7 h, the mixture was cooled to 60° C. and decompressed to 100 bar. A 600 g amount of di-n-butene (main constituents 14% octenes, 60% 3-methylheptenes, 26% 3,4-dimethylhexenes) was then added. After stirring for 10 minutes (1000 rpm), the mixture was left to stand for 15 minutes. The aqueous phase was separated. The di-n-butene phase contained cobalt carbonyls in a concentration of 0.019 by weight, calculated as cobalt. This solution was reacted at 170° C. and a synthesis gas pressure of 280 bar. The conversion was determined by the amount of absorbed synthesis gas. At 70% conversion the reaction was stopped. After cooling to 80° C. and decompression, cobalt was removed from the reaction mixture by adding 5% strength by weight aqueous acetic acid in the presence of air. The decobalted organic phase was separated by distillation into the fractions of residual olefin/small proportion of paraffin, aldehyde/alcohols and high-boiling components.

The residual olefin (175 g, main constituents about 4% octenes, 52% 3-methylheptenes, 44% 3,4-dimethylhexenes) was then reacted in a rhodium-catalyzed reaction in a fashion analogous to Example 1. The inert solvent added was 200 g of Texanol (2,2,4-trimethylpentanediol 1,3-monoisobutyrate), the rhodium concentration was adjusted to 200 ppm of Rh, and the molar ratio of ligand (tris(2,4-di-tert-butylphenyl) phosphite) to rhodium was 20/1. The pressure was constant at 50 bar, and the temperature was 130° C.

After 6 hours, the autoclave was cooled and decompressed, and the discharge was separated by distillation into the fractions of residual olefin/small amount of paraffin, aldehydes/alcohols and high-boiling components. The combined aldehyde/alcohol fractions from the two reactions were hydrogenated over Raney nickel to give the alcohols. The yield of alcohol over the two hydroformylation stages and hydrogenation was 87%.

Thus, according to the invention, a higher yield is achieved in a two-stage process than in a single-stage process (Comparative Example 6).

Example 3

(Improving Conversion, Reducing Byproducts)

The experiment was conducted in a pilot plant consisting of bubble-column reactor, a thin-film evaporator and a distillation device, which were connected as shown by numbers 1–8 in FIG. 1. Using this pilot plant, it was possible to investigate the essential aspects of conducting the process in two stages in the laboratory. The olefin to be hydroformylated was introduced into the bubble column at the bottom, together with an excess of synthesis gas and a high-boiling solvent containing the catalyst. Unreacted synthesis gas was removed at the top of the reactor. The liquid fractions (residual olefin, aldehyde, byproducts, high-boiling solvent, catalyst) were passed to the thin-film evaporator, which was operated under reduced pressure such that here the aldehyde formed was separated, together with the unreacted olefins, from the higher-boiling components in which the catalyst was dissolved. The high-boiling solvent used was dioctyl phthalate, which was present in the reactor in a proportion of 20% by weight. The rhodium concentration in the reactor was 100 ppm of rhodium, the ligand added was tris(2,4-di-tert-butylphenyl) phosphite, and the P/Rh ratio was 20/1. The bubble column was heated to a constant temperature of 120° C. externally via a twin-jacket, and the operating pressure was 50 bar of synthesis gas.

At the reaction conditions given above, an olefin feed of 2 kg/h of di-n-butene was established, and the bubble column had a volume of 2.1 liters. After a constant conversion level had become established, the material streams were balanced over a period of 100 hours. The mixture separated by means of the thin-layer evaporator was separated by distillation into unreacted olefins and the aldehydes formed. A 200 kg amount of di-n-butene gave 156 kg of aldehydes and 77 kg of olefin, which corresponds to an average conversion of 61.5%. At the same time, 130 g of high-boiling byproducts were formed, which became concentrated in the catalyst cycle.

The unreacted olefin in the first stage was reacted again in a second hydroformylation stage in the pilot plant. The reaction conditions corresponded to those of the first stage, except that the feed of olefin was reduced to 1 kg/h. The steady-state period selected was 77 hours, during which period of time exactly the 77 kg amount of olefin from the steady-state period of the first stage was reacted. A 65 kg amount of aldehydes was obtained. At the same time, 310 g of high-boiling byproducts were formed.

If the results of the two steady-state periods are summarized, then 221 kg of aldehydes were obtained from 200 kg of di-n-butene over a total of 177 operating hours. A 440 g amount of high-boiling byproducts was obtained in the process.

Example 4

(Comparative Example, Single-stage Hydroformylation)

In comparison to Example 3, 200 kg of di-n-butene were introduced into the pilot plant under otherwise identical experimental conditions over the course of 177 hours (1.13 kg (olefin)/h). A total of 198 kg of aldehyde was formed in the process. At the same time, 490 g of high-boiling byproducts were formed.

A comparison of Examples 3 and 4 shows that hydroformylation of the olefin in two stages over the same period using the same amount of olefin gives 23 kg of more aldehyde product. The result is that by dividing the hydroformylation reaction into two stages, better space-time yields are obtained than in the case of a single stage reaction. It is also found that in the two-stage procedure fewer high-boiling byproducts form overall, despite the higher conversion calculated over both stages. This is of particular importance, since the rhodium catalyst remains dissolved in the high-boiling components during the work-up of the hydroformylation mixtures. The more high-boiling components have to be removed, the more rhodium has to be replenished.

Example 5

Nonanols by Two-stage Hydroformylation of di-n-butene
1st Stage

In a 5 l high-pressure autoclave fitted with stirrer and electrical heating, 2000 g of di-n-butene (composition in Table 1, column 2) were hydroformylated in the presence of a cobalt catalyst at 175° C. and a synthesis gas pressure of 280 bar for 2 hours. The catalyst was prepared by treating 640 g of an aqueous cobalt acetate solution containing 1% by weight of cobalt with synthesis gas for 7 hours at 170° C. and 280 bar. After cooling and decompression, the cobalt carbonyls formed were transferred to the organic phase by extraction with the 2000 g of di-n-butene, and the organic phase was separated from the aqueous phase. The concentration of the catalyst in the di-n-butene was 0.020 by weight, based on di-n-butene and calculated as cobalt metal.

After cooling to 80° C. and decompression, the hydroformylation mixture was freed from cobalt by treatment with 5% strength by weight aqueous acetic acid in the presence of air. The decobalted hydroformylation mixture was separated from the aqueous phase.

The process was conducted four times under the same conditions. The decobalted hydroformylation mixtures were combined. A 9432 g amount of hydroformylation mixture was obtained; the composition according to GC analysis is given in Table 2, column 2. The analysis shows that the di-n-butene conversion was 67.2% and the selectivity of the product was 93.8%, corresponding to a yield of product of 63.1%. The products of value were considered here and below to be nonanals, nonanols and formates thereof.

2nd Stage

A 7500 g amount of decobalted hydroformylation mixture from the first stage was distilled over a column to recover unreacted olefins. The olefins were obtained as the top fraction, and the column bottoms contained the products of value and the high-boiling components. The isomer distribution in the recovered octene mixture is shown in Table 1, column 3. Compared with fresh di-n-butene containing 23% by weight of dimethylhexenes, the recovered olefin, containing 45% by weight of dimethylhexenes, contained considerably more of these unreactive olefins.

A 2000 g amount of recovered $C_8$-hydrocarbon mixture (91.75% by weight of $C_8$-olefins, 8.25% by weight of $C_8$-paraffins) was hydroformylated in the 5 liter autoclave of the first stage at 185° C. and a synthesis gas pressure of 280 bar for 3 hours. The cobalt catalyst was prepared as in the first stage and transferred to the olefin phase, its concentration being 0.050% by weight, based on the olefin and calculated as cobalt metal.

The hydroformylation mixture was cooled to 80° C., decompressed and decobalted as described in the first stage. This processing gave 2448 g of decobalted hydroformylation mixture whose composition by GC analysis is presented in Table 2, column 3. The olefin conversion was 91% and the selectivity to product was 83.7%, corresponding to a product yield of 76.2%.

The total olefin conversion over both stages was 97.2% at a selectivity to product of 90.7%, corresponding to a total product yield of 88.2%, based on di-n-butene used.

Example 6

(Comparative Example, Nonanols from Single-stage Hydroformylation of di-n-butene)

In the 5 l high-pressure autoclave employed in Example 5, 2000 g of di-n-butene (composition in Table 1, column 2) were hydroformylated in the presence of a cobalt catalyst at 185° C. and a synthesis gas pressure of 280 bar for 3 hours. The catalyst was prepared as described in Example 5. The concentration of the catalyst in the di-n-butene was 0.040% by weight, based on di-n-butene and calculated as cobalt metal.

After cooling to 80° C., the hydroformylation mixture was decompressed and freed from cobalt by treatment with 5% strength by weight aqueous acetic acid and air. Removal of the aqueous phase gave 2485 g of decobalted hydroformylation mixture whose composition determined by means of GC analysis is presented in Table 2, column 4. According to these data, a di-n-butene conversion of 92% was achieved, at a selectivity to product of 88.5%, corresponding to a yield of product of 81.4%.

Compared with a single-stage process (Example 6), considerably better conversions, selectivities and yields were achieved in the multistage process of the invention (Example 5).

TABLE 1

Isomer distribution in the feed olefin

| Olefins | Di-n-butene (starting material in Ex. 5, 1st stage and Ex. 6) % by weight | Octene mixture (starting material in Ex. 5, 2nd stage) % by weight |
|---|---|---|
| Dimethylhexenes | 23 | 45 |
| 3-Methylheptenes | 62 | 50 |
| n-Octenes | 15 | 5 |

TABLE 2

Composition of decobalted hydroformylation discharged (calculated on an $H_2O$-free basis)

| | Ex. 5, 1st stage % by weight | Ex. 5, 2nd stage % by weight | Ex. 6 % by weight |
|---|---|---|---|
| $C_8$-Olefins | 27.8 | 6.7 | 6.4 |
| $C_8$-Paraffins | 2.5 | 10.8 | 3.1 |
| $C_9$-Aldehydes | 48.8 | 45.2 | 52.7 |
| Nonyl formates | 2.2 | 5.7 | 4.2 |
| $C_9$-Alcohols | 17.4 | 22.9 | 26.9 |
| High-boiling compounds | 1.3 | 8.7 | 6.7 |

Obviously, numerous modifications and variations of the present invention are possible in light of the above teachings. It is therefore to be understood that within the scope of the appended claims, the invention may be practiced otherwise than as specifically described herein The disclosure of German priority patent Application Number 10034360.0 filed Jul. 14, 2000 is hereby incorporated by reference into the present application.

What is claimed as new and is intended to be secured by Letters Patent is:

1. A process for the multistage hydroformylation of olefins to give alcohols and/or aldehydes, which comprises in each stage:

a) hydroformylating olefins having a carbon atom content of 6 to 24 carbon atoms in the presence of a cobalt- or rhodium catalyst in a reactor to the point of conversion of olefin reactant to product of 20 to 98%;

b) removing the catalyst from the resulting liquid discharged from the reactor;

c) separating the resulting liquid hydroformylation mixture into a low-boiler fraction comprising olefins and paraffins, and a bottoms fraction comprising aldehydes and/or alcohols; and d) reacting the olefins present in the low-boiler fraction in subsequent process stages comprising steps a, b and c, and combining the bottoms fractions of process steps c) of all process stages.

2. The process as claimed in claim 1, wherein each process stage having hydroformylation step a), a catalyst removal step b) and a distillation step c) is conducted with the proviso that the catalyst separated in step b) is returned, directly or after work-up, to the hydroformylation step a) of each stage.

3. The process as claimed in claim 1, wherein each process stage having hydroformylation step a), a catalyst removal step b) and, apart from the last process stage, a distillation step c) is conducted with the proviso that the catalyst separated in b) is returned, directly or after work-up, to the hydroformylation step a) of each stage.

4. The process as claimed in claim 1, wherein each process stage having a hydroformylation step a) and a catalyst removal step b), provide liquid hydroformylation mixtures which are combined and distilled in a common distillation step c) thereby separating the combined materials into a low-boiler fraction and a bottoms fraction, with the proviso that the catalyst separated in steps b) is returned, directly or after work-up, to the hydroformylation steps a) of each of said stages.

5. The process as claimed in claim 1, wherein, for each process stage, the combined reactor discharge materials of all hydroformylation steps a) pass through only one catalyst removal step b) and one distillation step c), with the proviso that the catalyst separated in process step b) is divided, directly or after work-up, and returned to the hydroformylation steps a) of each of said hydroformylation stages.

6. The process as claimed in claim 1, wherein the at least one low-boiler fraction which contains paraffins is processed to partially or completely remove said paraffins therefrom.

7. The process as claimed in claim 1, wherein the bottoms fractions of a plurality of said stages are combined and distilled and then the distillate is hydrogenated.

8. The process as claimed in claim 1, wherein the bottoms fractions of a plurality of distillation steps c) are combined with the discharged material obtained from catalyst removal step b) and the combined material is hydrogenated.

9. The process as claimed in claim 1, wherein the aldehydes present in the bottoms fractions obtained and combined from several distillation steps c) are removed by distillation.

10. The process as claimed in claim 1, wherein the aldehydes present in the bottoms fractions obtained and combined of distillation step c) and present in the material discharged from catalyst removal step b) of the last process stage are removed by distillation.

11. The process as claimed in claim 1, wherein cobalt catalyst is employed in the hydroformylation step a) of each hydroformylation stage.

12. The process as claimed in claim 1, wherein rhodium catalyst is employed in hydroformylation step a) of each hydroformylation stage.

13. The process as claimed in claim 1, wherein in the hydroformylation step a) of a first hydroformylation stage, a cobalt catalyst is employed and in the hydroformylation steps a) of the other hydroformylation stages, a rhodium catalyst is employed.

14. The process as claimed in claim 1, wherein, in the hydroformylation step a) of a first hydroformylation process, a rhodium catalyst is employed and in the hydroformylation steps a) of the other hydroformylation stages, a cobalt catalyst is employed.

15. The process as claimed in claim 1, wherein the liquid materials discharged from at least one reactor of hydroformylation steps a) are homogeneous liquid phases.

16. The process as claimed in claim 1, wherein the cobalt or rhodium catalyst is dissolved homogeneously in the material discharged from liquid reactors of hydroformylation steps a).

17. The process as claimed in claim 1, wherein the olefins in the hydroformylation steps a) of a plurality of stages which follow the first hydroformylation stage are in each case hydroformylated to a conversion of at least 50%.

18. The process as claimed in claim 17, wherein the olefins in the hydroformylation steps a) of plurality of stages which follow the first hydroformylation stage are in each case hydroformylated to a conversion ranging from 55 to 98%.

19. The process as claimed in claim 1, wherein two complete hydroformylation processes are conducted.

* * * * *